(12) United States Patent
Kappler et al.

(10) Patent No.: US 9,078,625 B2
(45) Date of Patent: Jul. 14, 2015

(54) METHOD FOR TRANSFORMING INPUT DATA AND MEDICAL DEVICE

(75) Inventors: Steffen Kappler, Effeltrich (DE); Edgar Kraft, Erlangen (DE); Daniel Niederlöhner, Erlangen (DE); Thomas Reichel, Heroldsbach (DE); Karl Stierstorfer, Erlangen (DE); Helmut Winkelmann, Eggolsheim (DE)

(73) Assignee: SIEMENS AKTIENGESELLSCHAFT, Munich (DE)

( * ) Notice: Subject to any disclaimer, the term of this patent is extended or adjusted under 35 U.S.C. 154(b) by 670 days.

(21) Appl. No.: 13/328,198

(22) Filed: Dec. 16, 2011

(65) Prior Publication Data
US 2012/0158811 A1    Jun. 21, 2012

(30) Foreign Application Priority Data
Dec. 17, 2010   (DE) .......................... 10 2010 063 435

(51) Int. Cl.
*G06F 15/00*    (2006.01)
*A61B 6/00*     (2006.01)
*A61B 6/03*     (2006.01)

(52) U.S. Cl.
CPC .. *A61B 6/563* (2013.01); *A61B 6/03* (2013.01)

(58) Field of Classification Search
CPC .................. A61B 6/563; A61B 6/03
USPC ........................................ 708/203
See application file for complete search history.

(56) References Cited

U.S. PATENT DOCUMENTS

| 4,458,267 A | 7/1984 | Dolazza |
| 4,569,028 A | 2/1986 | Dolazza |
| 2002/0029264 A1* | 3/2002 | Ogino et al. .................. 709/223 |
| 2002/0141496 A1 | 10/2002 | Yang |
| 2005/0163314 A1* | 7/2005 | Bleichenbacher ............. 380/30 |
| 2010/0128949 A1 | 5/2010 | Wegener et al. |

FOREIGN PATENT DOCUMENTS

| CN | 1552043 A | 12/2004 |
| CN | 101099174 A | 1/2008 |
| CN | 201578258 U | 9/2010 |
| JP | 746408 | 2/1995 |
| WO | WO2007036608 A1 | 4/2007 |

OTHER PUBLICATIONS

Certified German Priority document for German Application No. 10 2010 063 435.2 (Not Yet Published).
(Continued)

*Primary Examiner* — Tan V. Mai
(74) *Attorney, Agent, or Firm* — Harness, Dickey & Pierce, P.L.C.

(57) ABSTRACT

A method is disclosed for transmitting measurement data from a transmitter system to a receiver system by way of a transmission link of a medical device. In an embodiment, the measurement data, as input data of a transformation method, is transformed to output values and, after transmission, back transformed again, the values of the input data lying between a maximum value and a minimum value and an assignment function being used for compression purposes, to allocate an output value to every value of the input data, a root function being used as the assignment function for at least some of the values.

15 Claims, 4 Drawing Sheets

(56) References Cited

OTHER PUBLICATIONS

"Root mean square"; Wikipedia http://en.wikipedia.org/w/index.php?title=Root_mean_square&oldid=401609984; 2010; GB; Dec. 10, 2010.

"Standardabweichung" aus Wikipedia; http://de.wikipedia.org/w/index.php?title=Standardabweichung&oldid=82251848; 2010; DE; Dec. 4, 2010.

John Marriner; ""Data Compression by Square Root of the Value""; 2003; US; Sep. 4, 2003.

Robert A et al.; "Square Root Data Compression"; AIP Review of Scientific Instruments; pp. vol. 74, No. 8; DOI: 10.1063/1.1593811; 2003; US; Aug. 1, 2003.

Chinese Office Action and English translation thereof dated Jun. 26, 2014.

* cited by examiner

METHOD FOR TRANSFORMING INPUT DATA AND MEDICAL DEVICE

PRIORITY STATEMENT

The present application hereby claims priority under 35 U.S.C. §119 to German patent application number DE 10 2010 063 435.2 filed Dec. 17, 2010, the entire contents of which are hereby incorporated herein by reference.

FIELD

At least one embodiment of the invention generally relates to a method for transmitting measurement data from a transmitter system to a receiver system by way of a transmission link of a medical device, in particular of an x-ray system. In at least one embodiment, the measurement data, as input data of a transformation method, is transformed to output values and, after transmission by way of the transmission link, back transformed again, the values of the input data lying between a maximum value and a minimum value and an assignment function being used for transformation purposes, to allocate an output value to every value of the input data. The invention also relates to a medical device and computer program products, which can be loaded directly into the memory of the transmit system or of the receiver system of a medical device.

BACKGROUND

During the performance of examinations using medical devices, e.g. CT systems, large quantities of data are generated in a very short time with the rotating detector, since the detector has a plurality of channels, which are read out at short sampling intervals during an examination. This data must be transmitted from the rotating part, the gantry of the CT system, or from the detector, by way of a transmission link to the non-rotating part of the CT system, i.e. to the image reconstruction facility, which creates the images to be reconstructed from this data. This transmission should proceed as quickly as possible, but at the same time there should be the smallest possible loss of signal quality for the data, e.g. any increase in noise due to the data transmission process. To design the transmission link, which has slip rings, between the rotating part and the non-rotating part as economically as possible in respect of bandwidth and capacity, it is necessary to reduce the quantity of data, for example by way of compression algorithms.

Currently the data for transmission from the gantry to the data processor is preprocessed so that an offset value is subtracted from the original 20-bit data of the analog/digital converter. The result is logarithmized by a transformation and thus scaled into a 16-bit data space. This process reduces the quantity of data significantly but there is what is known as a clipping of negative values. At high data speeds, e.g. with short sampling times or full detector utilization, an additional compression algorithm is used to compress the data further, so that the capacity of the available transmission link, i.e. the slip rings, is sufficient for the data transmission to keep pace during the examination. On the receiver side this additional compression is first reversed in what is known as a receiver, which is connected upstream of the data processor. The data is then forwarded to the data processor in a logarithmized data format. There, the data is then either further processed in logarithmic form or back transformed to the original linear scale, i.e. delogarithmized (exponentialized).

Although the provision of logarithmic data is highly suitable for further processing, i.e. image reconstruction, this procedure has the following disadvantages:
1. Noise can cause negative measurement values to occur with a low input signal. Since no real logarithm is defined for numbers less than or equal to zero, such values are set to a fixed value>zero (clipping). This means that during subsequent fusing (=combining of a number of adjacent pixels as part of image reconstruction) it is not possible to achieve satisfactory noise reduction.
2. There are specific correction algorithms, such as scatter beam correction, EFS filters, etc., in which, in addition to the logarithmic data, it is also necessary to represent the data on a linear intensity scale, i.e. provide linear data. The additional transformation of the logarithmized to linear data necessitates an unwanted additional time outlay.

SUMMARY

In at least one embodiment of the invention, an improved method is provided for transforming input data.

In embodiments of the invention, a method, a medical device and computer program products are disclosed.

With at least one embodiment of the inventive method, input data obtained using a medical device, e.g. a CT system, is transformed using an assignment function, which allocates an output value to every value of the input data. According to at least one embodiment of the invention, provision is made here for a root function to be used for at least one partial region of the values, which can lie between a minimum and a maximum value.

Accordingly a medical device of at least one embodiment, in particular an x-ray system, particularly preferably a CT system, has a transmitter system and receiver system connected to one another by a transmission link for the transmission of measurement data, which transforms the measurement data, as input data of a transformation, to output values and, after transmission by way of the transmission link, back transforms it again. The values of the input data lie between a maximum value and a minimum value and for the purposes of transformation an assignment function is used to allocate an output value to every value of the input data, with a root function being used according to the invention as the assignment function for at least some of the values between the minimum value and the maximum value.

A computer program product of at least one embodiment, which can be loaded directly into the memory of the transmit system, has program code segments, to perform a transformation of input data using a root function.

A second computer program product of at least one embodiment, which can be loaded directly into the memory of the receiver system, has program code segments to execute a back transformation of the transformed input data and/or optionally to output linearized data and/or logarithmized data to a data processor, such as an image reconstruction facility for example.

BRIEF DESCRIPTION OF THE DRAWINGS

The invention is described again in detail below with reference to the accompanying figures based on example embodiments.

DETAILED DESCRIPTION OF THE EXAMPLE EMBODIMENTS

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

Figure 1:
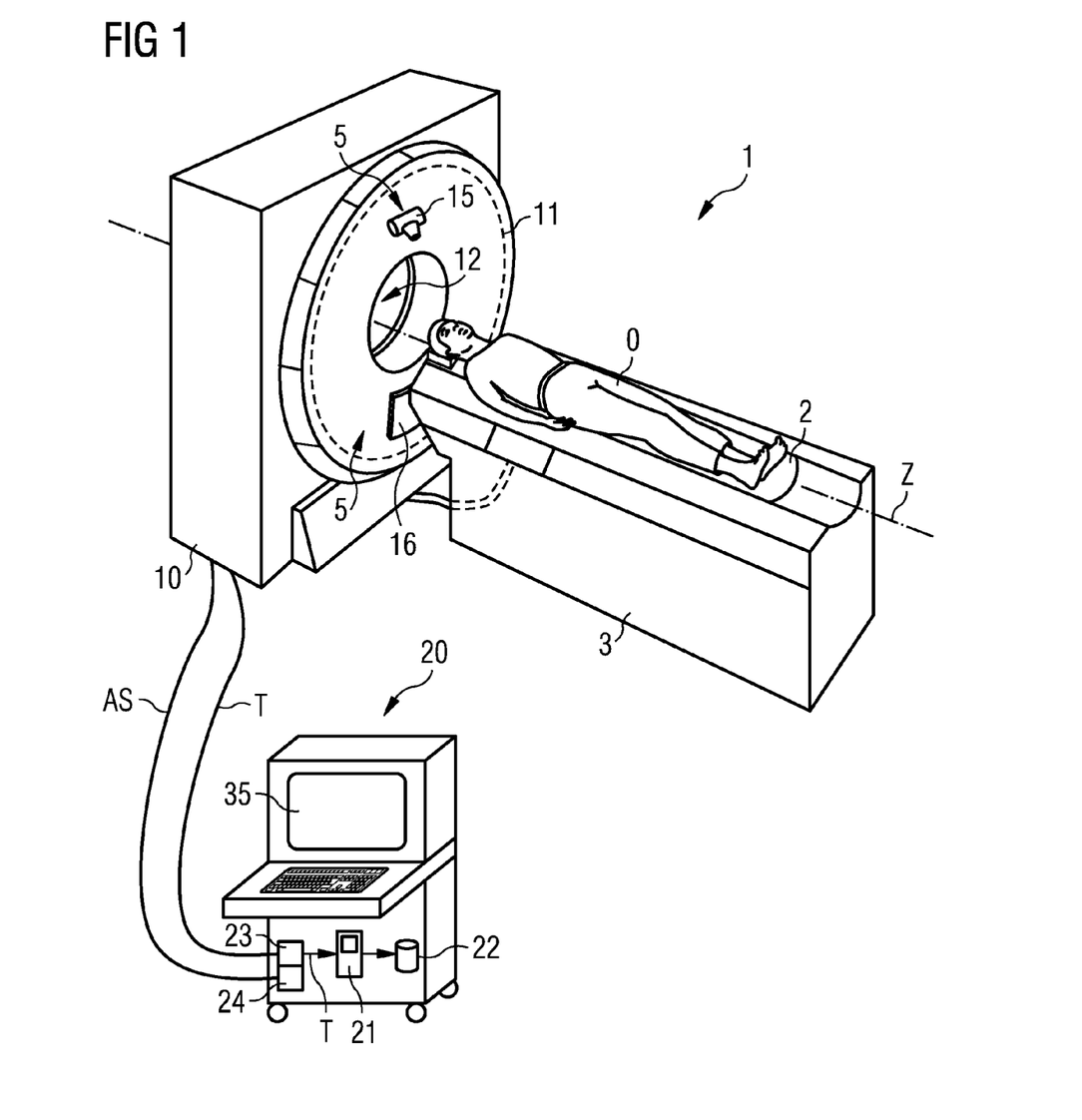
FIG. 1 shows a schematic diagram of an embodiment of an x-ray computed tomography system having an image reconstruction facility.

FIG. 1 first shows a schematic diagram of a medical device, in the present example embodiment a CT system 1, having an image reconstruction facility 21.

The CT system 1, as an example of an x-ray system, includes a standard scanner 10, in which a detector system 5, having a rotating detector 16 and an x-ray source 15 located opposite the detector 16, travels on a gantry 11 around a measurement chamber 12. Positioned in front of the scanner 10 is a patient support facility 3 or a patient table 3, the top part 2 of which can be moved, with a patient O positioned thereon, towards the scanner 10, in order to move the patient O through the measurement chamber 12 relative to the detector system 16. The scanner 10 and patient table 3 are activated by a control facility 20, from which acquisition control signals AS are emitted by way of a standard control interface 24, to activate the system as a whole according to predefined measurement protocols in the conventional manner. Moving the patient O along the z direction, which corresponds to the system axis z longitudinally through the measurement chamber 12, and at the same time moving the x-ray source 15 around means that the x-ray source 15 follows a spiral path relative to the patient O during the measurement. In this process the detector 16 always follows in a parallel manner opposite the x-ray source 15, to capture measurement data of the patient O as input raw data E, which is then used to reconstruct volume image data. A sequential measurement method can also be performed, wherein a fixed position is assumed in the z direction and then during a circuit, a partial circuit or a number of circuits the necessary input raw data E is captured at the relevant z position, to reconstruct a sectional image at this z position or to reconstruct a number of z position volume image data items from the input raw data E. The inventive method can in principle also be used with other medical devices, such as CT systems with a number of x-ray sources and/or detectors and/or with a detector forming a complete ring.

Figure 2:
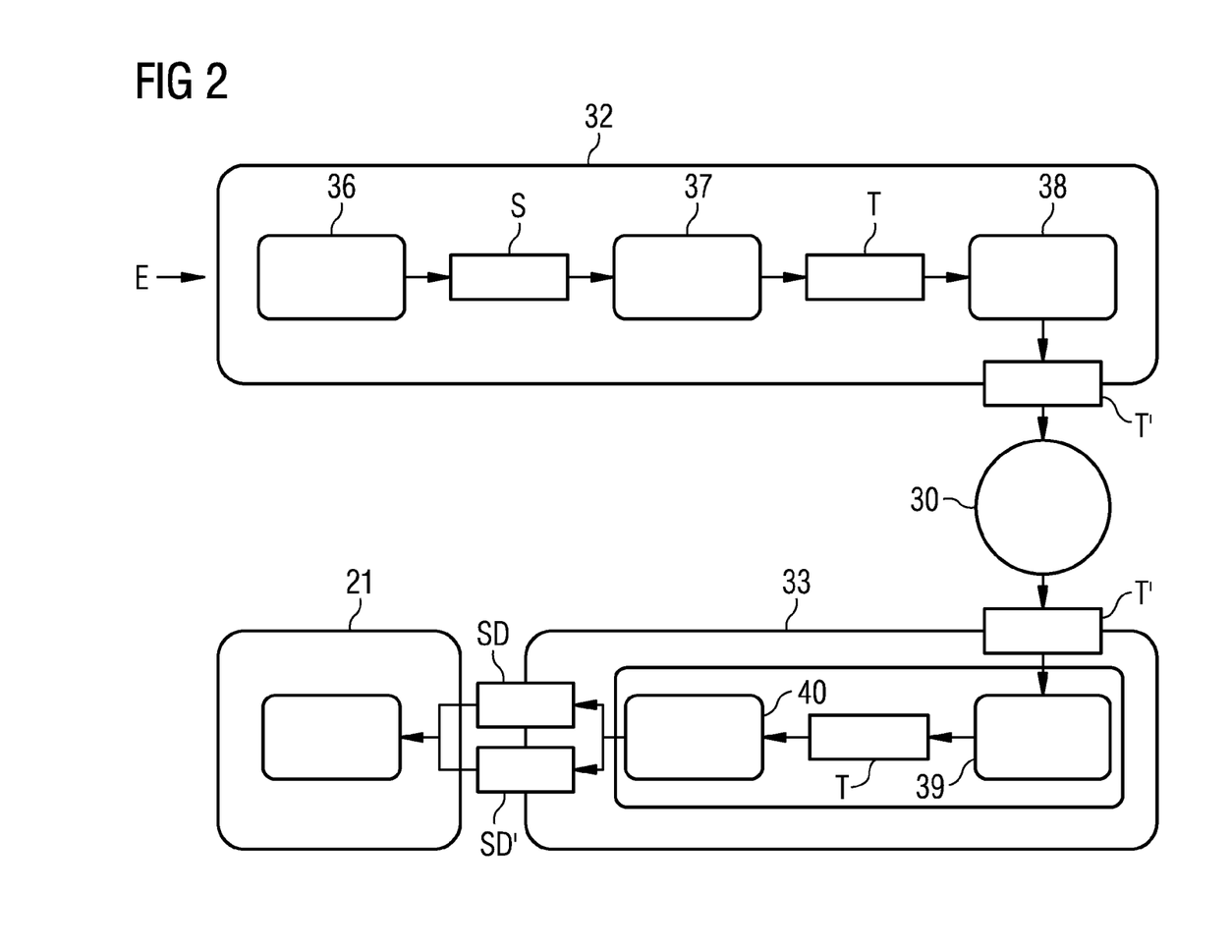
FIG. 2 shows a schematic diagram of the transformation and back transformation process.

Reference is now also made to FIG. 2.

The input raw data E captured by the detector 16 is fed to a data preprocessing system 32 of the CT system 1, which performs preprocessing, transformation and compression of the data.

To preprocess the input raw data E the data preprocessing system 32 has an AD converter and a unit for offset correction 36, which converts the input raw data E to linearized input data S with a 20 bits/pixel format.

To perform a transformation the data preprocessing system 32 has a first transformer 37 to transform the input data S to transformed data T according to an embodiment of the invention. To this end the first transformer 37 can have a processor with a programmable logic (FPGA).

A method for inventive transformation, according to which the transformer 37 preferably operates, is now described with reference to an example based on FIG. 3.

During the transformation in this example a low-value part D1 of the input data S is transformed according to the following equation (1), while the higher-value data D2 is transformed according to equation (2):

$$T = S + O_A \text{ for } S \leq P \quad (1)$$

$$T = \alpha \cdot \sqrt[n]{S - O_B} + O_C \text{ for } S > P \quad (2)$$

The following parameters are required for such a transformation method:

a bias value $O_A$ for the transformation of the low-value data D1, two shift values $O_B$, $O_C$, a scaling factor $\alpha$ and the degree n of the root function and for the transformation of the higher-value data D2, a value P, by which the switching point between the two equations (1) and (2) is defined.

First the degree n of the root function and the scaling factor $\alpha$ are defined. The maximum expected value and desired bit size of the compressed data T, e.g. 12 bits/pixel, are used for this purpose, with the size of the scaling factor $\alpha$ being determined therefrom, for example using a square root function. Higher order root functions can also be used, to achieve a higher degree of transformation.

The switching point P is then defined, at which the switch is made for values of the input data S from a first assignment function SQR to a second assignment function LIN. This takes into account the noise of evaluation circuits, as a result of which the input data can have negative values. A Gaussian distribution with a standard deviation can be assumed for the noise characteristic. A value is selected for the switching point P, which is sufficiently large in relation to the standard deviation. To ensure for example that at least 99% of the noise distribution lies in the linear function part, P would have to be at least three times as large as the standard deviation. This ensures that the noise signals are only transformed according to the linear assignment function, but not with the second assignment function SQR. A non-linear distortion of noise signals by the second assignment function SQR can thus be prevented.

The bias value $O_A$ is defined parallel to the switching point P. It is preferably selected so that its value is the same size as the value of the switching point P, so that the noise distribution lies symmetrically in the linear portion. In one alternative advantageous embodiment $O_A$ is selected as different from P, so that the probability of the occurrence of measurement values S with a value $<-O_A$ is acceptably low (for example $O_A$ could be a multiple of the standard deviation).

Finally the two shift values $O_B$, $O_C$ are defined. They are selected so that at the transition point between the two assignment functions LIN and SQR the slopes, i.e. the derivatives, are identical, i.e. there is a continuously differentiable transition between function parts.

Figure 3:
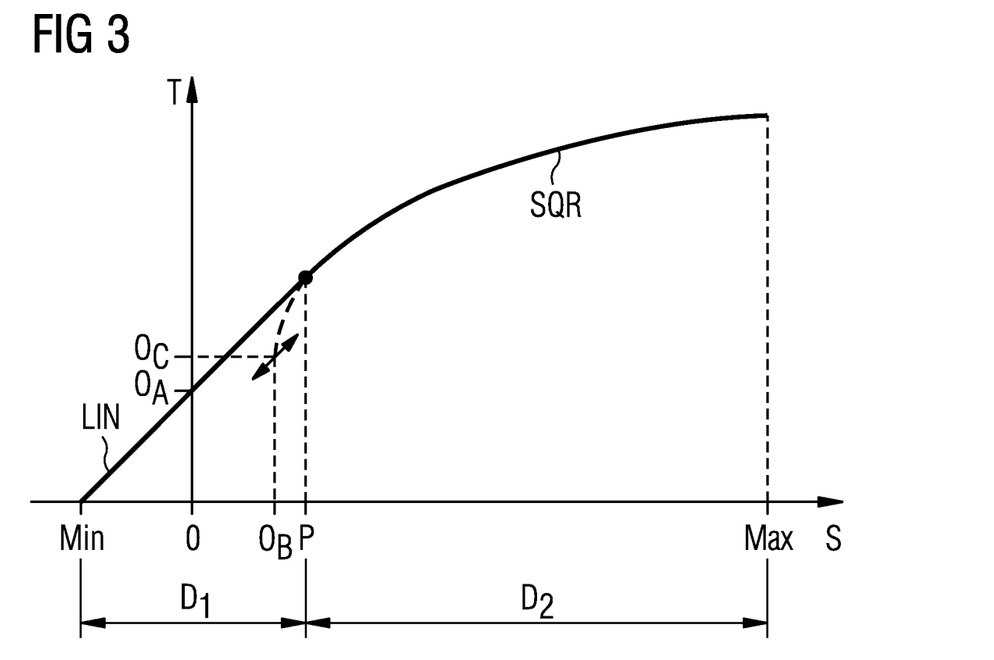
FIG. 3 shows a diagram of the composite assignment function.

In the example embodiment illustrated specifically in FIG. 3 a (preferred) square root function is used to transform the higher-value data D2. The general equation (2) can therefore advantageously be written as follows:

$$T = 2^{m-2} \sqrt{S - O_B} + O_C \text{ for } S > P \quad (2a)$$

For the scaling factor $\alpha$ here $\alpha = 2^m$ is set, where m is adjusted so that the transformation value $T_{max}$ of the highest possible measurement value $S_{max}$ is smaller than the value that can be shown as a maximum with the desired bit count (for 12 bits therefore $T_{max} < 4095 = 2^{12} - 1$).

With the assignment functions LIN and SQR illustrated in FIG. 3 the slope is greater in the region D1 of the input data S than in the region D2 of the root function SQR. Therefore for low values, i.e. in the region D1, of the input data S an unfalsified transformation with maximum accuracy is achieved by the linear function, while in the region of the higher-value input data S, i.e. in the region D2, the slope of the root function SQR is smaller than that of the linear function LIN, so that high values with long word lengths are increasingly compressed by the root function SQR.

The transformer 37 can be implemented so that it performs a static transformation, in which the bias value $O_A$, the shift value $O_B$, $O_C$ and optionally the scaling factor $\alpha$ as well as the degree n of the root function are generally set beforehand according to equation (2) and then not changed. In other words these are fixed values, which remain the same for all examinations. Alternatively a dynamic transformation can also take place, in which the bias value $O_A$, the scaling factor $\alpha$ and the shift values $O_B$, $O_C$ or individual ones of these cited values are redefined for every examination.

Reference is now made to FIG. 2 again.

The data preprocessing system 32 has a compressor 38, which performs a compression of the transformed data T, so that data T' transformed and compressed after the compression is present with a data volume of only 5-8 bits/pixel for example.

The transformed and compressed data T' is then transmitted by way of a data transmission link 34 from the data preprocessing system 32, which functions as a transmitter system, to a control facility 20, which has a receiver 33 serving as a receiver system for this purpose. Data transmission of transformed and compressed data T' therefore takes place from the data preprocessing system 32 as transmitter by way of the data transmission link 34 to a receiver 33.

The receiver 33 performs decompression of the transformed and compressed data T'. To this end the receiver 33 has a decompressor 39, which decompresses the transformed and compressed data T' to produce transformed data T, so that it is again present in a 12 bits/pixel format. To this end the decompressor 39 can have a processor with a programmable logic (FPGA).

For a back transformation of the data T transformed according to the invention a back transformer 40 is provided, which performs the method for transforming the input data S inversely, so that linearized data SD is again present in the original 20 bits/pixel format. The back transformer 40 can also be configured to supply back transformed, logarithmized data SD'. To this end the back transformer 40 can have a processor with a programmable logic (FPGA). Alternatively the decompression and back transformation can be performed by a processor.

Connected downstream of the receiver 33 is an image reconstruction facility 21, which in this example embodiment is implemented in the control facility 20 in the form of software on a processor.

The images reconstructed by the image reconstruction facility 21 are then stored in a memory 22 of the control facility 20 and/or output in the usual manner on a screen 35 of the control facility 20. They can also be fed by way of an interface (not shown in FIG. 1) into a network connected to the CT system 1, for example a radiological information system (RIS), and be stored in an accessible mass storage system there or be output on printers or filming stations connected thereto as images. The data can thus be further processed as desired and then stored or output.

Figure 4:
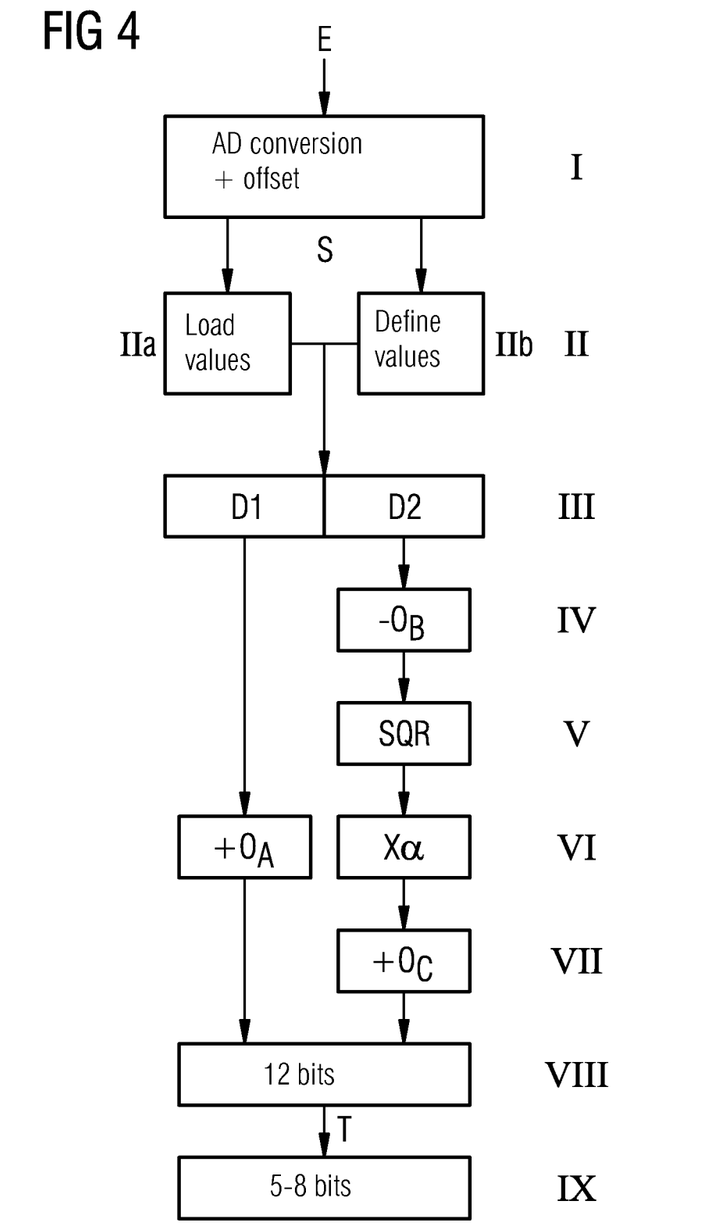
FIG. 4 shows a flow diagram of the transformation process.

The transformation process is described below with reference to FIG. 4.

First in a first step I the input raw data E is preprocessed. After an analog-digital conversion an offset correction takes place by subtracting a previously determined offset value. The result is linear, offset-corrected input data S in a 20 bits/pixel format.

The input data S is transformed using the inventive method.

For a static transformation according to equations (1) and (2a) in a step IIa the set values for the bias value $O_A$, the scaling factor $\alpha$ and the shift values $O_B$, $O_C$ and the switching point P are loaded from a memory (not shown). When a dynamic transformation is performed, in a step IIb the scaling factor $\alpha$, the switching point P and the bias value $O_A$, the shift values $O_B$, $O_C$ and the degree n of the root function are defined.

In a third step III the input data S in the present example embodiment with the value P is divided into a first region D1 and a second region D2. The values of the input data S in the region D1 are lower here than those of the input data S in the region D2.

In a fourth step IV the shift value $O_B$ is subtracted from the higher-value input data in the region D2 and in a fifth step V the resulting data is then transformed according to a square root function SQR and thereby compressed.

In a further, sixth step VI the bias value $O_A$ is added to the values of the region D1 and the root-extracted values of the region D2 are multiplied by the scaling factor $\alpha$. Then in a seventh step VII the shift value $O_C$ is added to the values of the region D2.

The two regions D1 and D2 are now combined again in an eighth step VIII and form the transformed data T. As a result the volume of the input data S has been reduced by the assignment function from 20 bits/pixel to 12 bits/pixel (data T).

In a ninth step IX data compression takes place, as already used in current standard medical devices, e.g. CT systems 1. Transformed and compressed data T' in a format having a volume of for example 5 to 8 bits/pixel is thus obtained from the transformed data T in a 12 bits/pixel format. The cited region for the bit count per pixel only refers to a typical assumed result of compression and should not be seen as restrictive. Values with a bandwidth of 4 bits/pixel or 11 bits/pixel can therefore readily occur in the compressed data T'. This circumstance is not referred to repeatedly below for the sake of simplicity.

To return to FIG. 2, the data transmission then takes place by way of the transmission link 34, in particular by way of the slip rings 30, to the receiver 33.

Decompression takes place there of the data T' present in the 5 to 8 bits/pixel format, so that 12-bit data T is obtained again from the 5 to 8-bit data. This compression reversal takes place in a processor/FPGA of the receiver 33.

In a further, second step the transformed 12-bit data T is back transformed again. In other words, an embodiment of the inventive transformation method is applied inversely. The data T here is transferred back into the original linear space (data SD) and/or logarithmized (SD'). The data SD, SD' can then be stored on the storage media 22 of the data processor 21.

The receiver 33 is configured to supply linear data or logarithmic data SD, SD' to the image reconstruction facility 21. It is therefore possible for filter operations to be performed directly with linear data SD in the image reconstruction facility 21, e.g. with the aid of adaptive filters. A back calculation from the logarithmic to the linear data space is therefore superfluous. The conversion of the data can take place fully encapsulated in a processor/FPGA of the receiver 33, allowing the image reconstruction facility 21 to operate directly with linear data SD. Alternatively the receiver 33 can logarithmize the linear data SD in the manner known to date, so that the data supplied to the image reconstruction facility 21 corresponds to the previously standard logarithmic format SD'. Logarithmizing can take place using look-up tables, which reduces computation outlay and thus the time required considerably. This establishes a downward compatibility with former systems. The receiver 33 is therefore configured to generate linear data SD and logarithmic data SD'.

By selecting a root function as at least part of the assignment function it is possible to adjust to the noise characteristic and therefore the information content of the detector signal, as the signal to noise ratio is to a large extent dominated by the photonic noise and is therefore a root function of signal size. The information content therefore remains almost unchanged but the necessary bandwidth for transmission is reduced and therefore brings about an adjustment to the channel capacity of the transmission link. Conversion of the data can be implemented simply by means of programmable logic, e.g. a Field Programmable Gate Array (FPGA). The unwanted clipping of data values is avoided by a further inventive feature, specifically the untransformed transmission of measurement values below a defined threshold. Reduction of the data volume to be transmitted by the transformation function allows further possibilities for savings in the medical device by better utilization of existing transmission capacities. This also allows for example medical devices with particularly large detectors to be realized, since the resulting larger quantities of data can also be transmitted without any problems. This method is also suitable primarily for quantum-counting detectors, since (untransformed) transmission is loss-free particularly in the lower activation region, i.e. for low measurement values.

One particular advantage of the root function is that the accuracy of the transformed data can be adjusted optimally to the information content of the input signal. This allows the data to be transmitted to have a reduced word width, e.g. 12 bits/pixel per sampling value instead of the previous 16 bits/pixel. In combination with a subsequent further data compression this reduction can bring about a disproportionate reduction of the data actually to be transmitted in the first step. The reason for this lies in the behavior of the compressor. If it behaves such that its saving (in bits/pixel) as a good approximation is only a function of the specific signal but not of the word width of the compressed data, the volume of data to be transmitted can be reduced disproportionately. If the compression saving in the specific instance is for example 5 bits/pixel, the data volume is reduced with a logarithmic transformation from 16 bits/pixel to 11 bits/pixel (69% of the initial volume) while with an inventive transformation it is reduced from 12 bits/pixel to 7 bits/pixel (58% of the initial volume).

Further advantageous embodiments and developments of the invention will emerge from the further dependent claims and the description which follows. The x-ray system or computer program products here can also be developed in the same manner as the dependent method claims.

Root functions of any degree, e.g. third or fourth degree, can be used. A square root function is preferably used, since the signal to noise ratio is a square root function of the number of x-ray quanta and the transformation is therefore ideally adjusted to the quantum noise. Therefore noise-induced signal deviations are not amplified disproportionately by the transformation.

A second assignment function that is different from the first assignment function can preferably be used as the assignment function (in addition to the root function as a first assignment function) for at least a second part of the values between the minimum value and the maximum value. A root function of a different degree or a suitable polynomial can be used as the second assignment function. Thus for example in an advantageous development a linear function can be used as the second assignment function. The linear function here can be used for a segment of the input values, which are lower than the input values for which the root function is used. This means that the compressed output values remain low, in particular for low values, thereby resulting in a decisive gain in the transformation factor. In other words a switching point between the two transmission functions is preferably set in respect of the input data, below which the input data is transformed according to the second assignment function and above which it is transformed according to the first assignment function.

In order to avoid negative values, which can result with the offset correction after an analog/digital conversion of the input raw data, a bias value is preferably added with the second assignment function, in particular linear function, the bias value being selected to be greater than zero. The value of the bias value is advantageously based on the strength of the noise of the raw data and is selected to be so large that negative values can only occur with a low, i.e. negligible, probability. If such an instance actually occurs, the value zero is transmitted instead of a negative value, having a negligible influence if the bias value is sufficiently large. Thus the clipping of negative values is avoided by adding a suitable bias value, without a sign bit being required, which would take up almost half of the dynamic region. This significantly improves the transformation where there is noise.

In particular with the root function it is possible, before or after applying said assignment function, to multiply the values by a scaling factor, the value of which is greater than zero. The scaling factor therefore has the effect that the transformation utilizes the available dynamic region to a maximum for a selected bit width. The powers of two that can be calculated very simply electronically are advantageous here. The value of the scaling factor $\alpha$ can preferably be selected as a function of the maximum and/or minimum value of the input data. For example the scaling factor $\alpha$ can be defined so that a maximum detector measurement value corresponds for example to a 12-bit value after the transformation. In this instance the scaling factor $\alpha$ is simply defined on the basis of possible maximum values. Alternatively however it is also possible to use the minimum value or other values between the minimum or maximum value to define the scaling factor $\alpha$. This allows adjustment to the value distribution of the input data, in particular when large parts of the input data have low values. If for example the expected maximum input value is at maximum beam intensity at a quarter of the value, the scaling factor can be increased correspondingly. It is then possible, in addition to clipping very negative input data, also to clip excessively high values, with the result that all the values beyond the clipping threshold are set to an identical value.

Therefore the specific values for the switching point between the two transmission functions and for the scaling factor are defined as a function of the desired bit width per pixel, the maximum possible measurement value of the input raw data and the selected bias value.

To achieve a continuous transition between the two assignment functions, provision is preferably made for a defined, constant shift value to be added to or subtracted from the values of the input data before application of the first assignment function, i.e. the root function. The shift value can have a positive or negative value. It is thus possible to move the first assignment function along a first axis to some degree.

Provision is also preferably made for a shift value to be added to or subtracted from the values of the input data after application of the first assignment function. The shift value can have a positive or negative value. It is thus possible to move the first assignment function along a second axis, which runs perpendicular to the first axis. It is thus possible to use the two shift values to move the first assignment function in two directions in the plane, so that the transition between the two assignment functions is continuous. There is therefore a unique assignment of input to output values without discontinuities at the transition point.

The transition between the first and second assignment function should preferably not only be continuous but also continuously differentiable. To this end the values for the shift values are preferably selected so that at the transition point from the first assignment function to the second assignment function the derivatives of the first assignment function and the second assignment function are identical. If therefore the second assignment function is for example a linear function with the slope 1, the root function is modified by the shift values so that the slope of the scaled root function at the switching point is also equal to 1.

The values for the bias value, the scaling factor, the shift values and the degree of the root function can be fixed, unchangeable values, which remain the same for what is known as a static transformation for every examination. Instead of such a static transformation a dynamic transformation can also be used, in which the values for one or all of the abovementioned values are redefined and reset for each examination. This allows better utilization of the channel capacity of the transmission link. With the dynamic transformation during configuration of the recording mode for example the controller of the CT system for example transmits the optimized scaling factor and/or the switching point or an equivalent configuration parameter to the data preprocessing system and the receiver of the medical device, e.g. a CT system. The bit width per pixel is not changed in this process.

If for example with a constant scaling factor and a switching point defined by the shift values, for adequate quality at high intensity 14 bits/pixel are required, at medium intensity 13 bits/pixel are required and at low intensity 12 bits/pixel are required, the x-ray system or CT system would have to be designed originally for 14 bits/pixel. The invention however allows an adequate quality to be achieved with 12 or 13 bits, which allows data compression to be dispensed with when the data transmission capacity of the transmission link is low.

The patent claims filed with the application are formulation proposals without prejudice for obtaining more extensive patent protection. The applicant reserves the right to claim even further combinations of features previously disclosed only in the description and/or drawings.

The example embodiment or each example embodiment should not be understood as a restriction of the invention. Rather, numerous variations and modifications are possible in the context of the present disclosure, in particular those variants and combinations which can be inferred by the person skilled in the art with regard to achieving the object for example by combination or modification of individual features or elements or method steps that are described in connection with the general or specific part of the description and are contained in the claims and/or the drawings, and, by way of combinable features, lead to a new subject matter or to new method steps or sequences of method steps, including insofar as they concern production, testing and operating methods.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program, tangible computer readable medium and tangible computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a tangible computer readable medium and is adapted to perform any one of the aforementioned methods when run on a computer device (a device including a processor). Thus, the tangible storage medium or tangible computer readable medium, is adapted to store information and is adapted to interact with a data processing facility or computer device to execute the program of any of the above mentioned embodiments and/or to perform the method of any of the above mentioned embodiments.

The tangible computer readable medium or tangible storage medium may be a built-in medium installed inside a computer device main body or a removable tangible medium arranged so that it can be separated from the computer device main body. Examples of the built-in tangible medium include, but are not limited to, rewriteable non-volatile memories, such as ROMs and flash memories, and hard disks. Examples of the removable tangible medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

It should finally be pointed out once again that the detailed methods and structures described above are exemplary embodiments and the basic principle can also be modified widely by the person skilled in the art, without departing from the scope of the invention, in so far as it is predefined by the claims. For the sake of completeness it should also be pointed out that the use of the indefinite article "a" does not exclude the possibility of the relevant features also being present in greater numbers.

What is claimed is:

1. A method for transmitting measurement data from a transmitter system to a receiver system by way of a transmission link of a medical device, comprising:
    transforming measurement data, as input data of a transformation method, to output values, the values of the input data lying between a maximum value and a minimum value and an assignment function being used for the transforming, to allocate an output value to every value of the input data and a root function being used as the assignment function for at least some of the values between the minimum value and the maximum value;
    sending the transformed measurement data over a transmission link; and
    back transforming the transformed measurement data after the sending, wherein
    the output values are multiplied by a scaling factor greater than zero before or after application of the assignment function, and
    the value of the scaling factor is selected as a function of the maximum value and the minimum value.

2. The method as claimed in claim 1, wherein the root function is a square root function.

3. The method as claimed in claim 2, wherein a second assignment function part that is different from a first assignment function part is used as the assignment function for at least a second part of the values between the minimum value and the maximum value.

4. The method as claimed in claim 1, wherein a second assignment function part that is different from a first assignment function part is used as the assignment function for at least a second part of the values between the minimum value and the maximum value.

5. The method as claimed in claim 4, wherein a linear function is used as the second assignment function part.

6. The method as claimed in claim 5, wherein a switching point is defined, at which the switch is made from the root function to the linear function for values of the input data, such that at least 99% of the noise distribution of the noise of the evaluation circuits lies in the linear function part.

7. The method as claimed in claim 6, wherein a value for the switching point is at least three times as large as the standard deviation of a Gaussian distribution for the noise distribution of the input data.

8. The method as claimed in claim 4, wherein the second assignment function is used with a bias value part.

9. The method as claimed in claim 4, wherein the shift values are selected so that at the transition point from the first assignment function part to the second assignment function part the derivatives of the first assignment function part and the second assignment function part are identical.

10. The method as claimed in claim 1, wherein a constant shift value is added to or subtracted from the values of the input data before application of a first assignment function part of the assignment function.

11. The method as claimed in claim 1, wherein a shift value is added to or subtracted from the values of the input data after application of a first assignment function part of the assignment function.

12. A computer program product, loadable directly into a memory of a transmitter system, having program code segments, to execute a transformation of input data according to the method as claimed in claim 1.

13. A computer program product, loadable directly into a memory of the receiver system, having program code segments, to at least one of execute a back transformation of the input data transformed as claimed in claim 1 and to output linear data or logarithmic data to a data processor.

14. The method of claim 1, wherein the medical device is an x-ray system.

15. A medical device, comprising:
a transmitter system; and
a receiver system, the receiver system and the transmitter system connected by a transmission link for the transmission of measurement data,
   the transmitter system configured to transform the measurement data, as input data of a transformation method, to output values using an assignment function to allocate an output value to every value of the input data, the values of the input data lying between a maximum value and a minimum value, the transmitter system further configured to use a root function as the assignment function for at least some of the values between the minimum value and the maximum value,
   the receiver system configured to back transform the output values to input values, wherein
the output values are multiplied by a scaling factor greater than zero before or after application of the assignment function, and
the value of the scaling factor is selected as a function of the maximum value and the minimum value.

* * * * *